United States Patent
Jones et al.

(10) Patent No.: US 9,815,781 B1
(45) Date of Patent: Nov. 14, 2017

(54) PROCESS FOR PREPARING 3-(METHYLSULFONYL)PROPIONITRILE

(71) Applicant: Olatec Therapeutics LLC, New York, NY (US)

(72) Inventors: Gerald S. Jones, Norwood, MA (US); Scott A. Goodrich, Stoughton, MA (US)

(73) Assignee: OLATEC THERAPEUTICS LLC, New York, NY (US)

( * ) Notice: Subject to any disclaimer, the term of this patent is extended or adjusted under 35 U.S.C. 154(b) by 0 days.

(21) Appl. No.: 15/045,447

(22) Filed: Feb. 17, 2016

Related U.S. Application Data

(60) Provisional application No. 62/118,035, filed on Feb. 20, 2015.

(51) Int. Cl.
*C07C 315/02* (2006.01)
*C07C 319/08* (2006.01)
*C07C 315/06* (2006.01)
*C07C 319/06* (2006.01)

(52) U.S. Cl.
CPC .......... *C07C 315/02* (2013.01); *C07C 315/06* (2013.01); *C07C 319/06* (2013.01)

(58) Field of Classification Search
CPC .... C07C 315/02; C07C 319/06; C07C 315/06
See application file for complete search history.

(56) References Cited

U.S. PATENT DOCUMENTS

2013/0225865 A1* 8/2013 St. Laurent ........... C07C 317/28
564/500

OTHER PUBLICATIONS

Aberkane et al. "Synthesis of Polysulfides, Sulfoxides and Sulfones Containing Reactive Groups" Phosphorous, Sulfur, Silicon Relat. Elem. 1993, 79, 245-246.*
Truce et al. "The Preparation of beta-Keto Sulfones by the Thorpe Reaction. The Acidity of beta-Keto Sulfones" Acta. Chem. Scand. 1953, 27, 2821-2828.*

* cited by examiner

*Primary Examiner* — Michael Barker
*Assistant Examiner* — Amanda L Aguirre
(74) *Attorney, Agent, or Firm* — Perkins Coie LLP; Viola T. Kung

(57) ABSTRACT

The present invention relates to processes for preparing for preparing 3-(methylsulfonyl)propionitrile. The processes comprise the steps of first reacting 2-chloroethyl methyl sulfide with sodium cyanide or potassium cyanide in a solvent or a solvent mixture to form 3-(methylthio)propionitrile, and then reacting the isolated 3-(methylthio)propionitrile with acetic anhydride, acetic acid, and hydrogen peroxide to form 3-(methylsulfonyl)propionitrile.

4 Claims, No Drawings

PROCESS FOR PREPARING 3-(METHYLSULFONYL)PROPIONITRILE

This application claims the benefit of U.S. Provisional Application No. 62/119,035, filed Feb. 20, 2015; which is incorporated herein by reference in its entirety.

FIELD OF THE INVENTION

The present invention relates to processes for preparing for preparing 3-(methyl sulfonyl)propionitrile.

BACKGROUND OF THE INVENTION 3-(Methylsulfonyl)propionitrile (CAS Registry 54863-37-5) is useful for treating inflammation and pain as described in U.S. Publication No. 2012-0157524, which is incorporated herein by reference in its entirety.

DETAILED DESCRIPTION OF THE INVENTION

The present invention is directed to a method for preparing 3-(methyl sulfonyl)propionitrile.

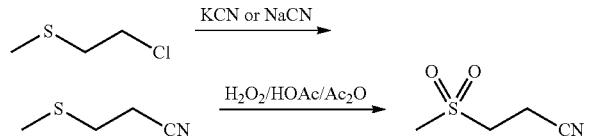

In a first embodiment, the method comprises the steps of: (a) mixing and reacting 2-chloroethyl methyl sulfide with sodium cyanide or potassium cyanide in a solvent or a solvent mixture at 20-100° C. for 4-24 hours, (b) separating the reaction mixture of (a) into an aqueous phase and an organic phase, (c) isolating 3-(methylthio)propionitrile in the organic phase, (d) mixing the isolated 3-(methylthio)propionitrile with acetic anhydride, acetic acid, and hydrogen peroxide at 25-42° C. to form 3-(methylsulfonyl)propionitrile, and (e) isolating 3-(methylsulfonyl)propionitrile from the reaction mixture of (d).

In a second embodiment, the method comprises the steps of: (a) mixing and reacting 2-chloroethyl methyl sulfide with sodium cyanide or potassium cyanide in a solvent or a solvent mixture at 20-100° C. for 4-24 hours, (b) separating the reaction mixture of (a) into an aqueous phase and an organic phase, (c) isolating 3-(methylthio)propionitrile in the organic phase, (d) mixing the isolated 3-(methylthio)propionitrile with acetic anhydride, (e) reacting the mixture of (d) with an aqueous solution comprising acetic acid, acetic anhydride and hydrogen peroxide at 25-42° C. to form 3-(methylsulfonyl)propionitrile, and (f) isolating 3-(methylsulfonyl)propionitrile from the reaction mixture of (e).

In the present method, 3-(methylthio)propionitrile (MTPN), which is a starting material for preparing 3-(methylsulfonyl)propionitrile, is prepared first in steps (a)-(c).

In step (a), liquid 2-chloroethyl methyl sulfide (A) is mixed with sodium cyanide or potassium cyanide (B) in a solvent or a solvent mixture. In general, sodium cyanide or potassium cyanide is in molar excess of 2-chloroethyl methyl sulfide. In one embodiment, the cyanide B is dissolved in water first, and then the sulfide A is mixed with the cyanide B in a solvent mixture of water and a water-miscible organic solvent such as ethanol, methanol, propanol, isopropanol, butanol, tetrahydrofuran, dioxane, acetonitrile or any mixture thereof. In another embodiment, the cyanide B is dissolved in water first, and then the sulfide A is mixed with B in a solvent mixture of water and a water-immiscible organic solvent such as ethyl acetate or diethyl ether to form a biphasic phase. In yet another embodiment, the sulfide A and the cyanide B are mixed in a polar organic solvent such as dimethylfuran, or dimethylformamide.

In step (a), the reaction time should be sufficient to allow the reaction to go to completion. In general, the reaction time is at least 4 hours, preferably at least 8 hours, for example, 4-24 hours, preferably 8-16 hours. The reaction temperature is 20-100° C., or 30-80° C., or 30-70° C., or 40-60° C. Higher temperatures in general speed up the reaction, but may cause more by-products. The reaction is carried out with sufficient mixing such that the reactants sulfide (A) is contacting with cyanide B during the reaction.

Upon completion of the reaction, the reaction mixture contains a mixture of the product 3-(methylthio)propionitrile, excess reagent sodium or potassium cyanide, and byproduct sodium or potassium chloride.

In step (b), the reaction mixture is allowed to settle and to separate into two phases: a lower aqueous phase and an upper organic phase containing MTPN. MTPN, which is less dense than water, accumulates in a layer above the surface of the water. Excess reagent sodium or potassium cyanide and by-product sodium or potassium chloride remain in the aqueous phase.

In step (c), the lower aqueous layer is discarded, and the upper organic phase of MTPN is obtained. The organic phase is optionally dried over solid sodium sulfate or magnesium sulfate to remove residual water and water soluble salts. The dried MTPN is isolated (for example, by vacuum filtration) as a clear, colorless oily liquid.

The intermediate MTPN is then oxidized to form the final product of 3-(methylsulfonyl)proprionitrile either by steps (d) of the first embodiment or by steps (d)-(e) of the second embodiment of the invention.

In the first embodiment, step (d) is mixing the isolated 3-(methylthio)propionitrile with acetic anhydride, acetic acid, and hydrogen peroxide at 25-42° C. to form 3-(methylsulfonyl)propionitrile.

In the second embodiment, the oxidation is carried out by two steps: (d) mixing MTPN with acetic anhydride, and (e) reacting the mixture of (d) with an aqueous solution comprising acetic acid, acetic anhydride and hydrogen peroxide at 25-42° C. to form the final product 3-(methylsulfonyl)propionitrile (MSPN). The reaction time is in general 1-4 hours, preferably 1-3 hours, or 1-2 hours In one embodiment, the MTPN is mixed with acetic anhydride at a molar ratio of 1:1-3, preferably about 1:2, and then slowly added to the reactor containing acetic acid, acetic anhydride and aqueous hydrogen peroxide (e.g., 20-40% w/v) while maintaining the temperature at 25-42° C., preferably 28-40° C., and more preferably 30-35° C.

After the oxidation reaction is completed, the final product MSPN is isolated from the reaction mixture by removing acetic acid and residual hydrogen peroxide. In one embodiment, the acetic acid and residual hydrogen peroxide are removed by distillation and/or rotary evaporation. After concentration, the product may be mixed with ethanol, heated and then cooled to 5-10° C. to effect crystallization. The product can be isolated by vacuum filtration and washed with cold ethanol to yield crystalline MSPN.

The following examples further illustrate the present invention. These examples are intended merely to be illustrative of the present invention and are not to be construed as being limiting.

EXAMPLES

Example 1: Preparing 3-(methylthio)propionitrile

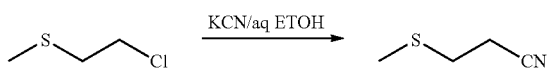

A mixture of 2-chloroethyl methyl sulfide (500 μL, 0.559 g, 5.06 mmol; TCI Lot ZIFDA [99.4% (GC)]), potassium cyanide (2 equivalent), potassium iodide (5 mol %), water (3 mL), and ethanol (3 mL) was stirred at 80° C. for 8 hours. The reaction mixture was filtered and the filtrate was concentrated to remove ethanol (rotavap/$T_{bath}$<30° C.). The residue was diluted with ether (about 10 mL) and the aqueous phase was removed by pipet. The ether phase was treated with $MgSO_4$ to remove water and activated charcoal to remove color, then vacuum filtered to give a clear colorless filtrate, which was concentrated to a clear, colorless oil: 0.369 g. GC-FID showed a major peak (93%) at the same retention time (6.82 min) as an authentic sample of 3-(methylthio)propionitrile.

Similar results were obtained when 1.3 equivalents of potassium cyanide were used, ethanol was replaced by tetrahydrofuran and potassium iodide was omitted, with or without catalytic Crown ether.

Example 2: Preparing 3-(methylsulfonyl)propionitrile

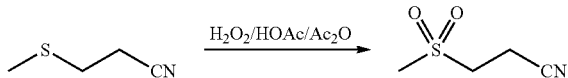

The product from Example 1 was used without further purification in this example.

To a solution of 3-(methylthio)propionitrile (0.360 g, 3.56 mmol) in acetic acid (1.5 mL) and acetic anhydride (1.5 mL), 30% hydrogen peroxide solution (4 equivalents) was added in 100 μL portions over 1 h. After stirring overnight, the reaction mixture was transferred to a watch glass (hood), and solvents were allowed to evaporate whereupon the residual liquid began to crystallize. The mixture was triturated with ethanol (about 10 mL), then vacuum filtered. The white solid was washed with cold ethanol, air-dried (0.363 g), then crystallized from hot ethanol: 0.310 g (the yield was 49% from 2-chloroethyl methyl sulfide); mp 70.5-72.5° C.; FTIR-ATR: the spectrum was in good agreement with reference standard of the title compound, but included three minor peaks; GC-MS: >99% purity.

What is claimed is:

1. A method for preparing 3-(methylsulfonyl)propionitrile, comprising the steps of:
    (a) mixing and reacting 2-chloroethyl methyl sulfide with sodium cyanide or potassium cyanide in a solvent mixture of water and a water-immiscible organic solvent at 20-100° C.,
    (b) allowing the reaction mixture of (a) to settle and to separate into an aqueous phase and an organic phase,
    (c) isolating 3-(methylthio)propionitrile in the organic phase,
    (d) mixing the isolated 3-(methylthio)propionitrile with acetic anhydride, acetic acid, and hydrogen peroxide at 25-42° C. to form 3-(methylsulfonyl)propionitrile, and
    (e) isolating 3-(methylsulfonyl)propionitrile from the reaction mixture of (d).

2. A method for preparing 3-(methylsulfonyl)propionitrile, comprising the steps of:
    (a) mixing and reacting 2-chloroethyl methyl sulfide with sodium cyanide or potassium cyanide in a solvent mixture of water and a water-immiscible organic solvent at 20-100° C.,
    (b) allowing the reaction mixture of (a) to settle and to separate into an aqueous phase and an organic phase,
    (c) isolating 3-(methylthio)propionitrile in the organic phase,
    (d) mixing the isolated 3-(methylthio)propionitrile with acetic anhydride,
    (e) reacting the mixture of (ii) with an aqueous solution comprising acetic acid, acetic anhydride and hydrogen peroxide at 25-42° C. to form 3-(methylsulfonyl)propionitrile, and
    (f) isolating 3-(methylsulfonyl)propionitrile from the reaction mixture of (e).

3. The method of claim 1, wherein the water-immiscible organic solvent is ethyl acetate or diethyl ether.

4. The method of claim 2, wherein the water-immiscible organic solvent is ethyl acetate or diethyl ether.

* * * * *